US00RE35609E

United States Patent [19]

Otani et al.

[11] E Patent Number: Re. 35,609

[45] Reissued Date of Patent: Sep. 16, 1997

[54] PROCESS FOR PURIFYING 2',3'-DIDEOXYNUCLEOSIDES

[75] Inventors: Masaru Otani; Toshiya Tanabe, both of Kawasaki, Japan

[73] Assignee: Ajinomoto Co., Inc., Tokyo, Japan

[21] Appl. No.: 385,888

[22] Filed: Feb. 9, 1995

Related U.S. Patent Documents

Reissue of:

[64] Patent No.: 4,962,193
Issued: Oct. 9, 1990
Appl. No.: 291,155
Filed: Dec. 28, 1988

U.S. Applications:

[62] Division of Ser. No. 191,370, May 9, 1988, Pat. No. 4,835,104.

[30] Foreign Application Priority Data

| | | | |
|---|---|---|---|
| Jun. 16, 1987 | [JP] | Japan | 62-149893 |
| Oct. 12, 1987 | [JP] | Japan | 62-257002 |
| Dec. 22, 1987 | [JP] | Japan | 62-324531 |
| Dec. 22, 1987 | [JP] | Japan | 62-324882 |

[51] Int. Cl.[6] ..... C07H 19/06; C07H 19/16; C07H 19/20; C07H 17/00; C07H 19/00; B01D 15/08

[52] U.S. Cl. ..... 536/22.1; 536/26.1; 536/26.73; 536/27.14

[58] Field of Search ..... 536/27.14, 127, 536/22.1, 26.1, 26.73; 210/656; 435/92

[56] References Cited

U.S. PATENT DOCUMENTS

| | | | |
|---|---|---|---|
| 4,058,659 | 11/1977 | Robins et al. | 536/28 |
| 4,207,308 | 6/1980 | Spenney | 514/169 |
| 4,323,573 | 4/1982 | Schaeffer | 514/261 |
| 4,464,466 | 8/1984 | Argoudelis et al. | 435/92 |
| 4,507,433 | 3/1985 | Miller et al. | 536/85 |
| 4,546,079 | 10/1985 | Metzger et al. | 435/71 |
| 4,725,677 | 2/1988 | Köster et al. | 536/28 |
| 4,754,026 | 6/1988 | Kawada et al. | 536/23 |
| 4,786,724 | 11/1988 | Letsinger | 536/29 |
| 4,788,181 | 11/1988 | Driscoll et al. | 536/23 |

FOREIGN PATENT DOCUMENTS

| | | | |
|---|---|---|---|
| 57-6917 | 2/1982 | Japan | 436/92 |

*Primary Examiner*—Stephanie W. Zitomer
*Attorney, Agent, or Firm*—Oblon, Spivak, McClelland, Maier & Neustadt, P.C.

[57] ABSTRACT

A biological process for producing a 2',3'-dideoxynucleoside from 2',3'-dideoxyuridine is disclosed. The 2',3'-dideoxynucleoside can be purified readily using a porous nonpolar resin absorbent.

16 Claims, No Drawings

PROCESS FOR PURIFYING 2',3'-DIDEOXYNUCLEOSIDES

Matter enclosed in heavy brackets [ ] appears in the original patent but forms no part of this reissue specification; matter printed in italics indicates the additions made by reissue.

This is a [continuation] division of application Ser. No. 07/191,370, filed May 9, 1988, *now U.S. Pat. No. 4,835,104.*

BACKGROUND OF THE INVENTION

1. Field of the Invention.

The present invention relates to processes for producing and purifying 2',3'-dideoxynucleosides, and to processes for producing 2',3'-dideoxy-2',3'-didehydronucleosides.

2. Discussion of the Background.

2',3'-Dideoxynucleosides and 2',3'-dideoxy-2',3'-didehydronucleosides display anti-viral activity but are prohibitively expensive to prepare industrially. For example, 2',3'-dideoxy-2',3'-didehydronucleosides of the formula (I):

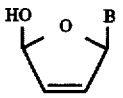

(I)

per se and 2',3'-dideoxynucleosides of the formula (II):

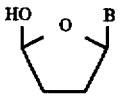

(II)

which can be obtained by reducing 2',3'-dideoxy-2',3'-didehydronucleosides, both display anti-viral activity and can be utilized, for example, in the treatment of AIDS.

Didehydronucleosides can therefore be used either as drugs or as intermediates for the production of drugs useful to combat viruses (cf, Published Unexamined Japanese Patent Application No. 280500/86 and J. Med Chem., 30, 440 (1987)). (The definition of substituent B is provided infra.)

Dideoxynucleosides, such as 2',3'-dideoxyadenosine [9-β- D-(2',3'-dideoxyribofranosyl)adenine]; 2',3'-dideoxyinosine [9-β- D-(2',3'-dideoxyribofranosyl) hypoxanthine]; and 2',3'-dideoxyguanosine [9-β- D-([2', 3'dideoxyribofranosyl)guanine], also possess powerful antiviral activity. All of these materials are therefore expected to be useful as antiviral medicines, particularly as drugs for the treatment of AIDS which is an intractable disease of worldwide concern.

2',3'-Dideoxy-2',3'-didehydronucleosides can be provided by a method which uses ribonucleosides as raw material (cf. J. Org. Chem., 39 (1974). Another method uses 2'-deoxyribonucleosides as raw materials (cf. J. Amer. Chem. Soc. 88, 1549 (1966) and J. Org. Chem., 32, 817 (1967)), etc.

The conventional method for producing 2',3'-dideoxynucleosides is by chemical deoxygenation of nucleosides at the 2' or 3' position, as described in Chem. Pharm. Bull., 22, 128 (1974). But reports on this method are very few however, and no industrial manufacturing process has yet been established on the basis of this basic method. The reasons for this are due to the facts that in this method (1) protective groups must be introduced prior to deoxygenation, (2) the reaction does not proceed smoothly because of the steric hindrance at the 2'- and 3'-positions, and (3) severe reaction conditions or powerful reagents cannot be used because nucelosides are unstable under such severe conditions. Nothing is so far known about a microbial process for producing 2',3'-dideoxynucleosides.

In all of these methods many steps are required and expensive materials must be used as the raw materials. The conventional chemical methods also have the problems that long reaction steps are involved and the product yield is low. These methods are consequently not advantageous from an industrial viewpoint. And hence, there has been a need for a new process for producing efficiently and inexpensively 2',3'-dideoxynucleosides in high yields.

There also has been a need for a method which can provide 2',3'-dideoxy-2',3'-didehydronucleosides industrially, efficiently and inexpensively using readily available starting materials.

In an available process for producing 2',3'-dideoxyinosine (DDI), the oxygen atom at the 2'- or 3'-position of the nucleoside is eliminated (see Chem. Pharm. BulL., 22, 128 (1974)). However, this process has not been used widely because (1) protective groups must be introduced prior to the reaction, and (2) the deoxygenation reaction tends to be hindered by severe steric hindrance at the 2'- and 3'-positions.

In cases where DDI is produced from microbial or enzymatic action on a substrate such as 2',3'-dideoxyuridine (DDU) or 2,3-dideoxyribose-1-phosphoric acid, the reaction mixture obtained contains, in addition to the desired product (DDI), unreacted DDU, hypoxanthine (Hyp), uracil (Ura) formed by the decomposition of the substrate, and small quantities of nucleic acids formed as by-products.

Known purification treatments, such as concentration and recrystallization, are not suited for obtaining efficiently high purity DDI from these mixtures. This is because impurities, such as Ura, Hyp, etc., have solubilities lower than that of the desired DDI and, consequently, the crystals of DDI which as formed are contaminated with the impurities. This makes the purification of DDI exceedingly difficult.

In addition to this, DDI is susceptible to hydrolysis under either acidic or neutral conditions. It is therefore difficult to purify DDI by means of ion exchange treatment since an acid is utilized for this treatment and, DDI is consequently hydrolyzed into a 2,3-dideoxyribose residue and a hypoxanthine residue.

For the above reasons, the purification and isolation of DDI has been practiced only in laboratories by means of repeated liquid cyromatography or thin layer chromatography. No commercial process for the purification of DDI is available. There has therefore been a need for an industrially advantageous purification process which makes it possible to efficiently and inexpensively purify DDI.

Another process has been reported in which 2',3'-dideoxyadenosine (DDA) is subjected to enzymatic deamination (see Biochim. Biophs. Acta., 566(2), 259 (1979). However, this deamination process, too, has not been practiced very often due to the reasons noted above.

Due to these difficulties, the isolation and purification of DDA has been practiced only in laboratories by means of repeated liquid chromatography. No commercial process for the purification of DDA is available.

In cases where DDA is produced either microbially or enzymatically from substrates such as 2, 3,-dideoxyuridiine (DDU) or 2,3-dideoxyribose-1-phosphoric acid, the reaction mixture obtained contains, in addition to the desired product (DDA), unreacted substrates, i.e., DDU and adenine ("Ad"), uracil ("U") formed by the decomposition of the substrate, and small quantities of nucleic acids formed as by-products.

Known treatments, such as concentration and recrystallization, are also not suited to obtain highly pure DDA efficiently. This is because both DDU and DDA have a high solubility and therefore could not be separated easily although Ad and U, solubilities of which are relatively small, can be removed by concentration to some extent.

In addition to this, DDA tends to be hydrolyzed under acidic conditions. It is therefore difficult to purify DDA using an ion exchange treatment since an acid is needed for elution of DDA and DDA is consequently hydrolyzed to a 2,3-dideoxyribose residue and an adenine residue.

In view of the advantageous properties of these materials there is thus a strongly felt need for both a more efficient process for their production and for an effective method for purifying the same.

SUMMARY OF THE INVENTION

Accordingly, it is an object of this invention to provide a process for the facile production of 2',3'-dideoxynucleosides.

It is another object of this invention to provide a facile process for the production of 2',3'-dideoxy-2',3'-didehydronucleosides.

It is another object of this invention to provide a process for the economical production of 2',3'-dideoxynucleosides.

It is another object of this invention to provide a process for the economical production of 2',3'-dideoxy-2',3'-didehydronucleosides.

It is another object of this invention to provide a process for the facile purification of 2',3'-dideoxynucleosides produced in a microbial process.

It is another object of this invention to provide a process for the purification of 2',3'-dideoxynucleosides produced in an enzymatic process.

The present invention thus provides processes which satisfy all of the above object of the invention and others which will become apparent from the description of the invention given hereinbelow.

In the process of producing 2',3'-dideoxynucleosides in accordance with the present invention, one can start from 2',3'-dideoxyuridine. The 2',3'-dideoxyuridine, phosphoric acid or a salt thereof, and a microorganism are combined in an aqueous medium. The microorganism used (1) belongs to one of the following genera: Escherichia, Flavobacterium, Serratia, Enterobacter, Erwinia, Citrobacter, Corynebacterium, Hafina, Kluyvera, Sarmonella or Xanthomonas, and (2) is capable of producing 2,3-dideoxyribose-1-phosphate from 2',3'-dideoxyuridine and phosphoric acid or a salt thereof. This first step produces 2,3-dideoxyribose 1-phosphate.

This 2,3-dideoxyribose 1-phosphate, an appropriate base, and a microorganism are combined in an aqueous medium. The microorganism used (1) belongs to the genera Escherichia, Flavobacterium, Serratia, Enterobacter, Erwinia, Citrobacter, Corynebacterium, Hafnia, Kluyvera, Sarmonella or Xanthomonas, and (2) is capable of producing the corresponding 2',3'-dideoxynucleoside from 2,3-dideoxyribose 1-phosphate and a base. The base is defined infra. This second step produces the desired 2',3'-dideoxynucleoside.

As should be clear from the above, in one of its aspects the present invention provides a two-component process. In the first component 2,3-dideoxyribose 1-phosphate is produced. In the second component a 2',3'-dideoxynucleoside is produced.

In another aspect of the present invention, a 2',3'-dideoxyuridine is obtained from uridine. In this aspect of the present invention, uridine is converted into a compound of the formula (III):

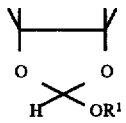

(III)

wherein $R^1$ is a $C_{1-12}$ alkyl group which may be linear, branched or cyclic. The compound of the formula (III):

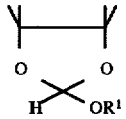

(III)

is then reacted with an acid anhydride to provide 2',3'-dideoxy-2',3'-didehydrouridine. This 2',3'-dideoxy-2',3'-didehydrouridine is then reduced to the corresponding 2',3'-dideoxyuridine. The 2',3'-dideoxyuridine, phosphoric acid or a salt thereof, a base, and a microorganism are then combined in an aqueous medium to obtain a 2',3'-dideoxynucleoside. The microorganism used (1) belongs to the genera Escherichia, Flavobacterium, Seratia, Enterobacter, Erwinia, Citrobacter, Corynebacterium, Hafnia, Kluyvera, Sarmonella or Xanthomonas, and (2) is capable of producing, from 2',3'-dideoxyuridine, phosphoric acid or a salt thereof, and a base, the corresponding 2',3'-dideoxynucleoside. The base used in this aspect of the present invention is defined infra.

Thus it should be clear from the above, that the present invention also provides a process for producing, on the one hand, 2',3'-dideoxyuridine from uridine, and, on the other hand, a process for producing a 2',3'-dideoxynucleoside from 2',3'-dideoxymuridine.

The present invention also provides a process for the purification of 2',3'-dideoxynucleosides, in particular 2',3'-dideoxynucleosides obtained from a microbial or enzymatic process, or combination thereof. In this purification process, the 2',3'-dideoxynucleoside is first adsorbed onto a porous nonpolar resin, the 2',3'-dideoxynucleoside is then isolated in its adsorbed form from unwanted contaminants, and the adsorbed 2',3'-dideoxynucleoside is then eluted from the porous nonpolar resin to obtain a pure product.

DETAILED DESCRIPTION OF THE PREFERRED EMBODIMENT

In a first embodiment the present invention provides a process for producing a 2',3'-dideoxynucleoside which comprises (1) contacting (1a) a microorganism. (1b) 2,3-dideoxyribose 1-phosphate and (1c) a base in an aqueous medium. The microorganism (i) is at least one member selected from the group consisting of the genera Escherichia, Flavobacterium, Serratia, Enterobacter, Erwinia, Citrobacter, Corynebacterium, Hafnia, Kluyvera, Sarmonella and Xanthomonas, and (ii) is capable of producing the corresponding 2',3'-dideoxynucleoside from 2,3-dideoxyribose 1-phosphate and a base.

In another embodiment of the present invention the 2,3-dideoxyribose 1-phosphate is obtained by contacting a microorganism, 2',3'-dideoxyuridine and phosphoric acid, or a salt thereof in an aqueous medium. The microorganism used (i) belongs to the genus Escherichia, Flavobacterium, Serratia, Enterobacter, Erwinia, Citrobacter, Corynebacterium, Hafnia, Kluyvera, Sarmonella and Xanthomonas, and (ii) is capable of producing 2,3-dideoxyribose 1-phosphate from 2',3'-dideoxyuridine and phosphoric acid or a salt thereof.

In another embodiment the present invention provides a process for producing a 2',3'-dideoxynucleoside by contacting a microorganism, 2',3'-dideoxyuridine, phosphoric acid or a salt thereof, and a base in an aqueous medium. The microorganism (i) belongs to the genus Escherichia, Flavobacterium, Serratia, Enterobacter, Erwinia, Citrobacter, Corynebacterium, Hafnia, Kluyvera, Sarmonella and Xanthomonas, and (ii) is capable of producing the corresponding 2',3'-dideoxynucleoside from 2',3'-dideoxyuridine, phosphoric acid or a salt thereof and a base.

In another embodiment the 2',3'-dideoxyuridine is obtained by (1) converting uridine into a compound of the formula (III)

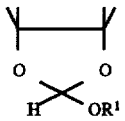

(III)

wherein $R^1$ is a $C_{1-12}$ alkyl group which is linear, branched or cyclic, and reacting the compound of formula (III) with an acid anhydride to obtain 2',3'-dideoxy-2,3'-didehydrouridine which is then (3) reduced to obtain 2',3'-dideoxyuridine.

As a result of extensive investigations to solve the problem outlined in the discussion of the background of the invention supra, the present inventors have found that didehydronucleosides having a basic skeleton of the by formula (IV):

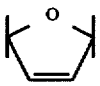

(IV)

can be readily produced in a high yield by converting compounds having a basic skeleton of the by formula (V):

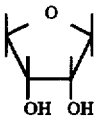

(V)

in the molecule thereof into compounds having a basic skeleton of the formula (III):

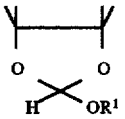

(III)

in the molecule thereof and then reacting the compounds of formula (III) with acid anhydrides at a temperature in the range of, for example, 20° to 200° C. On the basis of this finding, the present inventors have accomplished the present invention. In the formulae above, $R^1$ represents an alkyl group having 1 to 12 carbon atoms.

The compounds of formula (V) which one used as the starting materials of the present invention are, for example, compounds represented by general formula (VI):

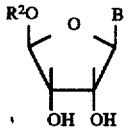

(VI)

The compounds of formula (III) are, for example, nucleoside derivatives represented by formula (VII):

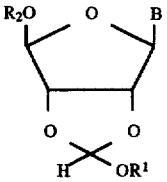

(VII)

In formulae (VI) and (VII) $R^1$ represents an alkyl group having 1 to 12 carbon atoms. $R^2$ represents a hydrogen atom, or an acyl group, an aralkyl group, a silyl group or the like. B represents a base bound to a ribose residue, such as a purine base bound at the 9-position thereof or a pyrimidine base bound at the 1-position thereof such as is known in nucleic acid chemistry.

The nucleoside derivatives of formula (VII) are reacted with acid anhydrides, for example, at temperatures of from 20° to 200° C., whereby 2',3'-dideoxy-2',3'-didehydronucleosides of formula (VIII):

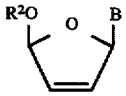

(VIII)

are obtained, where $R^2$ and B have the same meanings as provided above.

The nucleoside derivatives of formula (VII) can be prepared from compounds of formula (VI) using known techniques (cf. Tetrahedron, 23, 2301 (1967)).

In the formulae, $R^1$ represents an alkyl group. Examples of this alkyl group include methyl group, ethyl group, n-propyl group, etc. $R^2$ represents a hydrogen atom or, a $C_{1-6}$ acyl group, a $C_{7-14}$ aralkyl group, a silyl group or the like. B represents a base bound to a glucose residue, such as a purine base bound at the 9-position thereof or a pyrimidine base bound at the 1-position thereof.

Examples of the purine base include adenine, quanine, hypoxanthine, xanthine, 6-chloropurine, 6-mercaptopurine, 6-methylthiopurine, 2,6-dichloropurine, 2-chloropurine, 2,6-diaminopurine, 2-amino-6-chloropurine, 2-aminopurine, etc. Examples of the pyrimidine base include uracil, cytosine, thymine, 5-fluorouracil, 5-chlorouracil, 5-bromouracil, 5-iodouracil, 5-ethyluracil, 5-orotic acid, etc. In addition, other bases which can also be used include 5-amino-4-imidazolecarbonamide, 1,2,4-triazole-3-carboxamide, etc.

If necessary and/or desired, the amino group in the base moiety may be protected. The acid anhydrides which can be used in the present invention are not particularly limited but from a practical standpoint, anhydrides of fatty acids having 1 to 4 carbon atoms are preferred. In the reaction, it is sufficient to use the acid anhydride, but additional solvents may also be additionally used. The reaction temperature is between 20° and 200° C. The reaction time is 30 minutes to 24 hours.

The progress of the reaction can be tracked by thin layer chromatography or high performance liquid chromatography. After completion of the reaction, the desired didehydronucleosides of formula (VIII) can be isolated in a conventional manner such as by extraction, recrystallization or the like. If necessary, the didehydronucleosides of formula (VIII) can be further converted into 2',3'-dideoxy-2',3'-didehydronucleosides of formula (I):

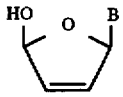

(I)

by removing the protective groups, or into 2',3'-dideoxynucleosides of formula (II).

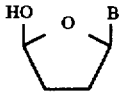

(II)

With the present invention didehydronucleosides can be produced in a simple manner and at low cost. Therefore, the present invention is extremely useful for the medical industry.

Intensive studies have led the inventors to find that 2',3'-dideoxynucleosides can be efficiently produced by enzymatic reaction .if 2',3'-dideoxyuridine or 2,3-dideoxyribose 1-phosphate (compounds which can be stably supplied at low costs by chemical synthesis) are used as the substrate. One embodiment of this invention was accomplished on the basis of these findings.

The reactions involved in the process of this invention may be illustrated as shown below:

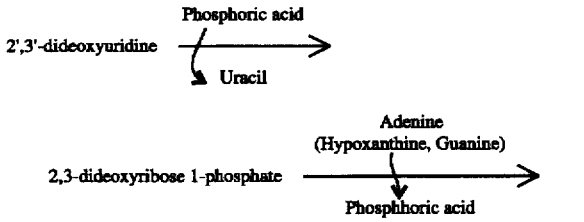

2',3'-dideoxyadenosine (2',3'-dideoxyinosine, 2',3'-dideoxyguanosine)

Thus an embodiment of this invention involves two types of reactions: (1) a process for producing 2',3'-dideoxynucleosides by the action of a microorganism upon 2,3-dideoxyribose 1-phosphate and a base; and (2) a process for directly producing 2',3'-dideoxynucleosides by the action of a microorganism upon 2',3'-dideoxyuridine, phosphoric acid or a salt thereof, and a base.

For example, the two types of reactions involved in the process of this invention are: (1) a process for producing 2',3'-dideoxyadenosine, 2',3'-dideoxyinosine or 2',3'-dideoxyguanosine by the action of a microorganism upon 2,3-dideoxyribose 1-phosphate and adenine, hypoxanthine or guanine; and (2) a process for directly producing 2',3'-dideoxyadenosine, 2',3'-dideoxyinosine or 2',3'-dideoxyguanosine by the action of a microorganism upon 2',3'-dideoxyuridine, phosphoric acid or a salt thereof, and adenine, hypoxanthine or guanine.

This invention also involves a process for producing 2,3-dideoxyribose 1-phosphate (a precursor of 2',3'-dideoxynucleosides) by the action of a microorganism upon 2',3'-dideoxyuridine and phosphoric acid or a salt thereof.

The microorganisms used in the process of this invention have both the enzymic activity to convert 2',3'-dideoxyuridine and phosphoric acid to 2,3-dideoxyribose 1-phosphate, and the enzymic activity to convert 2,3-dideoxyribose 1-phosphate and adenine, hypoxanthine or guanine to 2',3'-dideoxyadenosine, 2',3'-dideoxyinosine or 2',3'-dideoxyguanosine. Hence any one of these microorganisms can be used in any one of the above processes.

These are strains which belong to the genus Escherichia, Flavobacterium, Serratia, Enterobacter, Erwinia, Citrobacter, Corynebacterium, Hafnia, Kluyvera, Sarmonella or Xanthomonas. The following may be mentioned as illustrative examples of these microorganisms:

| | |
|---|---|
| Escherichia coli | ATCC 10798 |
| Flavobacterium rhenanum | FERM BP-1862 |
| Serratia rubefaciencs | FERM BP-1863 |
| Enterobacter aerogenes | ATCC 13048 |
| Erwinia carotovora | FERM BP-1538 |
| Citrobacter freundii | ATCC 8090 |
| Corynebacterium vitarumen | ATCC 10234 |
| Hafnia alvei | ATCC 9760 |
| Kluyvera citrophila | FERM P-1349 |
| Sarmonella schottmuelleri | ATCC 8759 |
| Xanthomonas citri | FERM BP-1861 |

2',3'-Dideoxynucleosides, or 2,3-dideoxyribose 1-phosphate which is an intermediate therefor, may be formed by the action of a microorganisms listed above either by the culture method in which microorganism is cultivated in the presence of the substrates, or by the enzyme react ion method in which grown cells of said microorganism or a treated product thereof are allowed to act upon the substrates.

In the culture method, a commonly employed medium containing carbon sources, nitrogen sources, inorganic ions such as P, S, Fe and Mn, and as required trace nutrients, such as vitamins, and organic nitrogen sources, such as protein decomposition products and yeast extract, is used as a basal medium. When, for example, 2,3-dideoxyribose 1 phosphate is to be produced, 2',3'-dideoxyuridine and phosphoric acid (or a salt thereof) are added to this basal medium.

When producing, for example, 2',3'-dideoxyadenosine, 2',3'-dideoxyinosine or 2',3'-dideoxyguanosine from 2,3-dideoxyribose 1-phosphate, 2,3-dideoxyribose 1-phosphate and adenine, hypoxanthine or guanine are added the above basal medium.

When, for example, 2',3'-dideoxyadenosine, 2',3'-dideoxyinosine or 2',3'-dideoxyguanosine is to be produced directly from 2',3'-dideoxyuridine, 2',3'-dideoxyuridine, phosphoric acid (or a salt thereof) and adenine, hypoxanthine or guanine are added to the above basal medium.

The substrates may be added to the culture medium either at the start of or during cultivation.

In the enzyme reaction method, various kinds of enzyme sources my be used. These include a culture solution obtained after cultivation of a microorganism in a commonly employed medium containing carbon sources, nitrogen sources, inorganic ions such as P, S, Fe and Mn, and as required trace nutrients, such as vitamin, and organic nitrogen sources, such as protein decompositions products and yeast extract; microbial cells separated from said culture solution; and a treated product thereof (for example, microbial cells dried by the use of acetone, cell debris, ultrasonicated cells, cells treated with toluene or a surface-active agent, cells treated with an enzyme such as lysozyme, protein fraction isolated from cells by extraction followed by salting-out and other purification steps, purified protein fraction having the activity for the intended enzyme reaction, and immobilized products of the microbial cells and treated products thereof).

The preferable concentration of 2',3'-dideoxyuridine or 2,3-dideoxyribose 1-phosphate used as a substrate is in the range from 1 to 1000 mM. When producing 2,3-dideoxyribose 1-phosphate, the amount of phosphoric acid or a salt thereof to be added is at least equimolar to that of 2',3'-dideoxyuridine (preferably 1 to 10 molar proportions); when producing a 2',3'-dideoxynucleoside, on the other hand, its mount is smaller than the above (preferably 0.01 to 10 molar proportions) because the acid is recycled in the reaction system. Any type of phosphoric acid salt that does not retard the reaction can be used, illustrative examples including inorganic salts, such as Na, K, $NH_4$' Ca and Mg salts, and organic salts such as trimethylammonium salt.

Suitable amount of the base (adenine, hypoxanthine or guanine) to be added is at least equimolar to that of 2',3'-dideoxyuridine or 2,3-dideoxyribose 1-phosphate (preferably 1 to 10 molar proportions), when producing 2',3'- dideoxyadenosine , 2',3'-dideoxyinosine or 2',3'-dideoxyguanosine directly from 2',3'-dideoxyuridine and when producing 2',3'-dideoxyadenosine, 2',3'-dideoxyinosine or 2',3'-dideoxyguanosine from 2,3-dideoxyribose 1-phosphate.

In the direct method starting from 2',3'-dideoxyuridine, however, the amount of base may be less than equimolar, when unreacted substrate (2',3'-dideoxyuridine), if left in the reaction mixture, offers no problem in the succeeding purification step.

2,3-Dideoxyribose 1-phosphate used as a substrate may be a commercially available product, a product prepared by chemical synthesis, or a product produced from 2',3'-dideoxyuridine by microbial action and isolated from the culture solution (as disclosed in this invention).

To an aqueous solution containing these substrates, are added the aforementioned microbial cells or a treated product thereof, and the reaction is allowed to proceed by holding the mixture at 20° to 70° C. (preferably 40° to 70° C.) controlled pH in the range from 4 to 10, thus accumulating, in the culture solution, a 2',3'-dideoxynucleoside (final product) or 2,3-dideoxyribose 1-phosphate (intermediate).

The 2',3'-dideoxynucleoside (final product) or 2,3-dideoxyribose 1-phosphate (intermediate) can be recovered from the culture solution by known techniques (for example, by utilizing the difference in solubility in water and organic solvents, and by the use of ion-exchange and adsorption resins). The amounts of these compounds can be determined by high-performance liquid chromatography.

The process of this invention produces 2',3'-dideoxyadenosine, 2',3'-dideoxyinosine and 2',3'-dideoxyguanosine at higher yields by simple operations, as compared to conventional, chemical synthetic methods.

2',3'-Dideoxyadenosine (DDA), 2',3'-dideoxyinosine (DDI) and 2',3'-dideoxyguanosine produced by the process of this invention have powerful antiviral action, and are therefore expected to be useful as antiviral agents, particularly for the treatment of AIDS which is an intractable disease of worldwide concern.

The inventors have now also found that DDI can be separated from such impurities Ura, Hyp, etc. when a crude DDI solution, after being subjected, e.g., to a treatment for removing cells, a treatment for removing proteins and/or a treatment for decolorization, is treated with a porous nonpolar resin, preferably in combination with crystallization and separation steps.

Accordingly, there is provided in another embodiment of the present invention a process for the purification of DDI which is characterized in that, upon the purification of DDI produced with the action of a microorganism or an enzyme or purification of crude DDI derived therefrom, said DDI is adsorbed on a porous nonpolar resin. Preferably the adsorption step is carried out in combination with a crystallization step.

Any crude DDI can be purified in accordance with the process of the invention, irrespective of its purity. For example, a solution resulting from a reaction where a 2,3-dideoxyribose residue is bonded to a hypoxanthine residue with the action of a microorganism or an enzyme, or a crude purification product thereof, can be purified.

Any microorganisms capable of producing DDI can be utilized in the present invention, including those belonging to such genera as Escherichia, Flavobacterium, Serratia, Enterobacter, Erwinia, Citrobacter, Corynebacterium, Hafnia, Fluyvera, Salmonella, Xanthomonas, and the like. There are no particular limitations on the enzymes which can be used. Any enzymes contained in the above-mentioned microorganisms, as well as other enzymes having the same function, can be utilized.

Reaction mixtures containing DDI to be treated in accordance with the process of the invention may contain any impurities, including DDU, Hyp, Ura and nucleic acids formed as by-products. There are no particular limitations on the concentration of DDI to be contained in the mixture to be treated, provided that it is within its solubility.

Porous nonpolar resins usable in the process of the invention include styrene-divinylbenzene copolymers and derivatives thereof modified, e.g., with halogens so as to increase the specific gravity thereof. Examples of such copolymers include Diaion HP series and SP series (manufactured by Mitsubishi Chemical Industries Co., Ltd.), XAD-4 (manufactured by Rohm & Haas Co.) and OC 1031 (manufactured by Bayer AG). Any other porous nonpolar resins having properties similar to those mentioned above can be used in the process of the invention. In particular, those having a high specific gravity, for example, SP 207 (manufactured by Mitsubishi Chemical Industries Co., Ltd.) can be advantageous in the respect of their operability since such resins do not float at the time a DDI-containing solution is fed.

The contact between a porous nonpolar resin and a DDI-containing solution can be effected by either a batch method or a column method. A column method can be advantageous in terms of easiness in operation.

There are no particular limitations on the rate of passing solutions through the column. In ordinary cases, a space velocity (SV) of from 0.5 to 4.0, in particular, from 1 to 2, can be preferable.

The volume load of the DDI-containing solution to be fed to the column depends on the concentration of DDI contained in the solution. A resin load of DDI of from 5 to 40 g/1-R, in particular, from 10 to 30 g/1-R, can be preferred with regard to separability and economical efficiency.

The temperature of the solution passed through the column can be in the range of from 10° to 50° C. In this temperature range, there are almost no substantial differences in the separability of DDI and such impurities as Hyp and Ura, which are contained in the solution.

With regard to the stability of DDI, the pH of the solution to be fed to the resin is preferably on the alkaline side, in particular, in the range of from 8.0 to 10.0. A temperature not higher than 50° C. can also be preferable in respect of its stability.

Explanation will hereinafter be given on the method for eluting DDI from the column. An aqueous solution of a lower fatty alcohol can be suited as an eluent. For example, there can be used aqueous solutions of methyl alcohol, ethyl alcohol, isopropyl alcohol or the like. The elution can be carried out at ordinary space velocity (SV), e.g., of from 1to 2.

The purification procedure utilizing a porous nonpolar resin can be practiced as follows. A predetermined amount of a DDI-containing solution is fed to a column charged with a porous nonpolar resin, and Ura and Hyp are eluted by passing water through the column. DDI and DDU are then eluted by an aqueous alcohol solution.

Thereafter, the fraction that contains DDI and DDU are concentrated and then cooled, so as to separate DDI from DDU through crystallization. A highly pure DDI can be obtained in this manner.

If the pH of the concentrated solution is maintained on the alkaline side, preferably, in the range of from 8 to 10, the decomposition of the DDI can be prevented at the time of crystallization and, hence, the yield of crystallization can be improved.

If desired, other treatments, such as solvent extraction and liquid chromatography, can be applied thereto, in addition to the treatments described hereinabove.

As described hereinabove, DDI can be separated and purified in an effective manner by the treatment with a porous nonpolar resin according to the invention, preferably in combination with crystallization. It is therefore highly expected that the process be industrially practiced.

The inventors have now also found that impurities, such as Ad, U, DDU, etc., can be separated from DDA and that highly pure DDA can be obtained from a DDA-containing fermentation or enzymatic solution, after that solution has been subjected, e.g., to a treatment for removing cells, a treatment for removing proteins and/or a treatment for decoloration, has been concentrated and filtered, and the filtrate is then treated with a porous nonpolar resin. Another embodiment of this invention has been completed on the basis of the above finding.

Accordingly, there is provided in an embodiment of the present invention a process for the purification of DDA which is characterized in that, upon the purification of DDA produced with the action of a microorganism or an enzyme, the DDA is adsorbed by a porous nonpolar resin.

Any crude DDA can be purified in accordance with the process of the invention, irrespective of its purity. For example, a solution resulting from a reaction where a 2,3-dideoxyribose residue is bonded to an adenine residue with the action of a microorganism or an enzyme, or a crude purification product thereof, can be purified.

Any microorganisms capable of producing DDA can be utilized in the present invention, including those belonging to such genera as Escherichia, Flavobacterium, Serratia, Enterobacter, Erwinia, Citorobacter, Corynebacterium, Hafnia, Fluyvera, Salmonella, Xanthomonas, and the like. There are no particular limitations on the enzymes which can be used. Any enzymes contained in the above-mentioned microorganisms, as well as other enzymes exhibiting the same function, can be utilized.

Concentrated DDA-containing solutions which can be treated in accordance with the process of the invention may contain any impurities, including DDU, Ad, U and nucleic acids formed as by-products. There are no particular limitations on the concentration of the solution to be treated, provided that the DDA is dissolved.

Porous nonpolar resins usable in this embodiment of the invention include styrene-divinylbenzene copolymers and derivatives thereof modified, e.g., with halogens so as to increase their specific gravity. Examples of such copolymers include Dialon HP series and SP series (manufactured by Mitsubishi Chemical Industries, Ltd.), XAD-4 (manufactured by Rohm & Haas Co) and OC 1031 (manufactured by Bayer AG). Any other porous nonpolar resins having properties similar to those mentioned above can be used in this embodiment of the invention. In particular, those having a high specific gravity, for example, SP 207 (manufactured by Mitsubishi Chemical Industries, Ltd.) can be advantageous in the respect of their operability since such resins do not float at the time when a concentrated DDA-containing solution is fed.

The contact between a porous nonpolar resin and a concentrated DDA-containing solution can be effected by either a batch method or a column method. A column method can be advantageous with regard to the easiness in operation.

There are no particular limitations on the rate of passing solutions through the column. In ordinary cases, a space velocity (SV) of from 0.5 to 4.0, in particular, from 1 to 2, can be preferable.

The volume load of the concentrated DDA-containing solution to be fed to the column depends on the concentration of DDA contained .in the solution. A resin load of DDA of from 5 to 40 g/l-R, in particular, from 10 to 30 g/l-R, can be preferred with regard to separability and economical efficiency.

The temperature of the solution to be passed through the column can be in the range of from 10° to 50° C. In this temperature range, there are almost no substantial differences in the separability of DDA and such impurities as Ad, U and DDU, which my be contained in the concentrated solution.

In the method for eluting DDA from the column, an aqueous solution of a lower fatty alcohol can be suitably used as an eluent. For example, there can be used aqueous solutions of methyl alcohol, ethyl alcohol, isopropyl alcohol or the like. The elution can be carried out at ordinary space velocity (SV), e.g., of from 1 to 2.

The actual purification procedure utilizing porous nonpolar resin can be practiced as follows. A predetermined amount of a concentrated DDA-containing solution is fed to a column charged with a porous nonpolar resin, and U is eluted by passing water through the column. Thereafter, DDU and Ad are eluted by an aqueous alcohol solution, and DDA is then eluted by passing an aqueous alcohol solution having a higher-alcohol concentration. The filtrate that contains DDA is concentrated and then cooled, so as to obtain highly pure DDA.

Other features of this invention will become apparent in the course of the following descriptions of exemplary embodiments which are given for illustration of the invention and are not intended to be limiting thereof.

EXAMPLE 1: Production of 2',3'-dideoxy-2',3'-didehydrouridine

To 50 ml of acetic anhydride was added 5.00 g (17.5 mmols) of 2',3'-o-methoxymethylideneuridine at room temperature with stirring. The solution was heated to 140° C. and kept at this temperature for 5 hours under reflux of the solvent. After cooling to room temperature, the solvent was removed by distillation under reduced pressure, 50 ml of water was added, and the mixture was extracted 3 times with 100 ml of chloroform. The extract was concentrated under reduced pressure, 30% ammonia water was added and the resultant mixture was stirred at room temperature for an hour. The solvent was again removed by distillation under reduced pressure and purification was performed by silica gel column chromatography to give 3.02 g 14.4 mmols) of the title compound (yield 82.3%) mp 150.0°–151.0° C.; $\lambda_{max}$(MeOH) 260 nm (ε9980), $\lambda_{min}$(MeOH) 231 m (ε3980); $^1$H-NMR ($Me_2SO$-$d_6$) δ 3.58 (d, 1H, J=5.13 Hz), 3.59 (d, 1H, J=5.13 Hz), 4.78 (m, 1H), 4.98 (t, 1H, J=5.13 Hz), 5.59 (d, 1H, J=8.05 Hz), 5.92 (d, 1H, J=5.86 Hz), 6.40 (d, 1H, J=5.86 Hz), 6.82 (m, 1H), 7.75 (d, 1H, J=8.05 Hz), 11.31 (brs, 1H); Fast atom bombardment mass spectrum m/z 211 (MH+). Anal. Calcd for $C_9H_{10}N_2O4$: C, 51.43; H, 4.80; N, 13.33. Found: C, 51.32; H, 4.81; N, 13.31.

REFERENCE EXAMPLE 1: Production of 2',3'-o-methoxymethylideneuridine

To 1 liter of tetrahydrofuran were added 50 g (0.205 mols) of uridine, 112 ml (1.03 mols) of methyl orthoformate and 10 g (52.6 mmols) of paratoluenesulfonic acid at room temperature with stirring. After stirring at room temperature for 24 hours, the reaction mixture was poured into an aqueous sodium bicarbonate solution followed by extraction with chloroform 5 times. The extract was dried over sodium sulfate and concentrated to give 49.5 g (0.173 mmols) of 2',3'-o-methoxymethylideneuridine (yield, 84.5%).

REFERENCE EXAMPLE 2: Production of 2',3'-dideoxyuridine

A solution of 2',3'-dideoxy-2',3'-didehydrouridine (1.0 g, 4.8 mmol) in methanol (10 ml) containing a catalyst (wet 5% palladium on carbon) (400 mg) was stirred in an atmosphere of hydrogen for 1 h. The catalyst was removed by filtration and the filtrate was concentrated. The residue was chromatographed on silica gel ($CHCl_3$/MeOH=5/1) to give 2',3'-dideoxyuridine (0.99 g, 97% yield): Mp 121.2°–121.7° C.; $\lambda_{max}$(MeOH) 262 nm ($\epsilon$10560), $\lambda_{min}$(MeOH) 232 nm ($\epsilon$3810); $^1$H-NMR ($Me_2O$-$d_6$)$\delta$ 1.74–2.00 (m, 3H), 2.20–2.35 (m, 1H), 3.49–3.55 (m, 1H), 3.64–3.69 (m, 1H), 4.00–4.03 brs, 1H), 5.03 (s, 1H), 5.58 (d, 1H, J=8.06 Hz), 5.95 (m, 1H), 7.94 (d, 1H, J=8.06 Hz), 11.25 (brs, 1H); Fast atom bombardment mass spectrum m/z 213 (MH+). Anal. Calcd for $C_9H_{12}N_2O_4$: C, 50.94; H, 5.70; N, 13.20. Found: C, 50.95; H, 5.71; N, 13.20.

EXAMPLE 2: Production of 2',3'-dideoxyadenosine, 2',3'-dideoxyinosine and 2',3'-dideoxyguanosine Fifty milliliters of a culture medium (pH 7.0), containing 0.5 g/dl yeast extract, 1.0 g/dl peptone, 1.0 g/dl meat extract and 0.5 g/dl NaCl, was placed in 500-m flasks each and sterilized. To each of the flasks, was inoculated a pinch (Aze) of a microorganism listed in Table 1, which had previously been grown in a bouillon medium at 30° C. for 16 hours, and shake culture was continued at 30° C. for 16 hours. The grown cells were separated from the culture solution by centrifugation, washed with a 0.05 M phosphate buffer (pH 7.2), and centrifuged again.

The washed microbial cells thus obtained were added to 10 ml of a 0.05 M Tris buffer (pH 7.2) containing 20 mM 2,3-dideoxyribose 1-phosphate and 20mM adenine (or 20mM hypoxanthine, or 20mM guanine) to a concentration of 5%, and the mixture was held at 60° C. for 24 hours.

The concentration of 2',3'-dideoxyadenosine, 2',3'-dideoxyinosine or 2',3'-dideoxyguanosine formed in each of the reaction mixtures was measured by high-performance liquid chromatography.

TABLE 1

| Strains | 2',3'-Dideoxynucleosides formed (mg/dl) | | |
|---|---|---|---|
| | 2',3'-Dideoxy-adenosine | 2',3'-Dideoxy-inosine | 2',3'-Dideoxy-guanosine |
| Escherichia coli ATCC 10798 | 302 | 290 | 285 |
| Flavocaterium rhenanum FERM BP-1862 | 152 | 148 | 151 |
| Serratia rubefaciencs FERM BP-1863 | 81 | 62 | 49 |
| Enterobacter aerogenes ATCC 13048 | 25 | 26 | 27 |
| Erwinia carotovora FERM BP-1538 | 172 | 191 | 186 |
| Citrobacter freundii ATCC 8090 | 43 | 29 | 35 |
| Corynebacterium vitarumen ATCC 10234 | 36 | 39 | 42 |
| Hafnia alvei ATCC 9760 | 41 | 46 | 40 |
| Kluyvera citrophila FERM P-3149 | 44 | 41 | 43 |
| Salmonella schottmuelleri ATCC 8759 | 39 | 40 | 36 |
| Xanthomonas citri FERM BP-1861 | 51 | 48 | 50 |

EXAMPLE 3

Washed cells of microorganisms listed in Table 2, which had been grown and treated.-in the same way as in Example 1, were added to 10 ml of a 100mM phosphate buffer (pH 7.0) containing 20mM 2',3'-dideoxyuridine to a concentration of 5%, and the mixture was heated at 60° C. for 24 hours. The concentration of 2,3-dideoxyribose 1-phosphate formed in each of the reaction mixtures was measured by means of high-performance liquid chromatography. The results are also shown in Table 2.

TABLE 2

| Strain | 2,3-Dideoxyribose 1-phosphate formed (mg/dl) |
|---|---|
| Escherichia coli ATCC 10798 | 108 |
| Flavocaterium rhenanum FERM BP-1862 | 72 |
| Serratia rubefaciencs FERM BP-1863 | 23 |
| Enterobacter aerogenes ATCC 13048 | 18 |
| Erwinia carotovora FERM BP-1538 | 91 |
| Citrobacter freundii l ATCC 8090 | 47 |
| Corynebacterium vitarumen ATCC 10234 | 36 |
| Hafnia alvei ATCC 9760 | 29 |
| Kluyvera citrophila FERM P-3149 | 45 |
| Sarmonella schottmuelleri ATCC 8759 | 28 |
| Xanthomonas citri FERM BP-1861 | 37 |

EXAMPLE 4

Washed cells of microorganisms listed in Table 3, which had been grown and treated in the same way as in Example 2, were added to 10 ml of a 100 mM phosphate buffer (pH 7.0) containing 20 mM, 2,3-dideoxyribose 1-phosphate and 20 mM adenine (or 20 mM hypoxanthine, or 20 mM guanine) to a concentration of 5%, and the mixture was held at 60° C. for 24 hours. The concentration of 2',3'-dideoxynucleoside formed in each of the reaction mixtures was measured by means of high-performance liquid chromatography. The results are shown in Table 3.

TABLE 3

| Strains | 2',3'-Dideoxynucleosides formed (mg/dl) | | |
|---|---|---|---|
| | 2',3'-Dideoxy-adenosine | 2',3'-Dideoxy-inosine | 2',3'-Dideoxy-guanosine |
| Escherichia coli ATCC 10798 | 239 | 202 | 213 |
| Flavocaterium rhenanum FERM BP-1862 | 131 | 138 | 130 |
| Serratia rubefaciencs FERM BP-1863 | 64 | 58 | 61 |
| Enterobacter aerogenes ATCC 13048 | 21 | 28 | 29 |
| Erwinia carotovora FERM BP-1538 | 165 | 188 | 174 |
| Citrobacter freundii ATCC 8090 | 44 | 32 | 38 |
| Corynebacterium vitarumen ATCC 10234 | 35 | 31 | 29 |
| Hafnia alvei ATCC 9760 | 40 | 35 | 38 |
| Kluyvera citrophila FERM P-3149 | 41 | 38 | 36 |
| Salmonella schottmuelleri ATCC 8759 | 38 | 36 | 40 |
| Xanthomonas citri FERM BP-1861 | 47 | 43 | 41 |

EXAMPLE 5

Escherichia Coli (ATCC 10798) was grown in the same medium as used in Example 2 at 37° C. for 16 hours in the same manner as in Example 2, 5 ml of a previously sterilized 500mM phosphate buffer containing 200mM 2',3'-dideoxyuridine and 200mM hypoxanthine was added to the above culture solution, and cultivation was continued for an additional 10 hours. Measurement by means of high-performance liquid chromatography showed formation of 36 mg/dl of 2',3'-dideoxyinosine.

EXAMPLE 6

Washed cells of Escherichia coli (ATCC 10798) grown and treated in the same way as in Example 2 were added to 10 ml of a 10mM phosphate buffer (pH 7.0) containing 100 mM 2',3'-dideoxyuridine and 100 mM adenine to a concentration of 2%, and the mixture was incubated at temperatures shown in Table 4 for 24 hours. The concentration of 2',3'-dideoxyadenosine formed in each of the reaction mixtures was measured by means of high-performance liquid chromatography. The results are shown in Table 4.

TABLE 4

| Reaction temp. (°C.) | 2',3'-Dideoxyadenosine formed (mg/dl) |
|---|---|
| 40 | 611 |
| 45 | 923 |
| 50 | 1048 |
| 55 | 673 |
| 60 | 262 |

EXAMPLE 7

Into shouldered 500 ml flasks was charged 50 ml each of a culture medium (pH =7.0) containing 500 mg/dl of a yeast extract, 1,000 mg/dl of peptone, 1,000 mg/dl of a meat extract and 500 mg/dl of NaCl, and the flasks were sterilized. One platinum loopful of Escherichia coli (ATCC 10798), which had been cultured on a bouillon agar medium at 30° C. for 16 hours, was inoculated in each medium contained in the flasks and cultured with shaking at 30° C. for 16 hours. The cells were separated from the medium by centrifugation and washed with 0.05 M phosphate buffer (pH=7.0). The cells were again separated by centrifugation to prepare washed cells.

The washed cells of Escherichia coil ATCC (10798) were added to 1 liter of 1 mM phosphate buffer (pH=7.0) were added to containing 20 mM of DDU and 20 mM of Hyp, the concentration of the cells in said medium being 1% by weight. The reaction was allowed to proceed at 50° C. for 24 hours. As a result, there was produced 70 mg/dl of DDI (recovering rate=15%).

The cells were removed off by centrifugation (at 7,000 G for 40 minutes), and then 50 mg of activated carbon (Shirasagi Charcoal, manufactured by Takeda Chemical Industries Co., Ltd.) was added after adjustment to pH=8.0 by NaOH solution thereto. The resulting mixture was maintained at 50° C. for 1 hour, in order to remove off proteins and to effect decoloration, and then filtered, using a filter having a pore size of 0.45 μm. The pH of the filtrate was adjusted to 8 by the use of 1N NaOH, and the filtrate was then concentrated to 100 ml. The thus concentrated solution was fed (at SV=1) to a column (having a diameter of 20 mm and a height of 210 mm) charged with 65 g of a porous nonpolar adsorption resin (SP 207, manufactured by Mitsubishi Chemical Industries, Ltd.) and then 300 ml of water was passed through the column (at SV=2). The thus obtained fraction is designated as Fraction I. Thereafter, 260 ml of aqueous 20% ethyl alcohol solution was passed through the column (at SV=2) to carry out elution. The fraction obtained is designated as Fraction II. The above treatments with said resin were carried out at a temperature of 30° C.

The fractions were analyzed by liquid chromatography. In Fraction I were contained Ura and Hyp, which were recovered at a percentage of 99% and 98%, respectively. In Fraction II were contained DDI and DDU, which were recovered at a percentage of 98% and 95%, respectively.

The pH of Fraction II was adjusted to 8 by the addition of 1N NaOH, and it was then concentrated to crystallize DDI. There was obtained 410 mg of crystals of highly pure DDI. The results of elemental analysis of the thus obtained DDI are shown in Table 5.

TABLE 5

| | Elemental Analysis | | |
|---|---|---|---|
| | C | H | N |
| Calculated: | 50.84% | 5.12% | 23.72% |
| Found: | 50.86% | 5.12% | 23.91% |

EXAMPLE 8

To a column having a diameter of 20 mm and a height of 210 mm and charged with 65 ml of a porous nonpolar adsorption resin (SP 207, manufactured by Mitsubishi Chemical Industries, Ltd.) was fed (at SV=2) 100 ml of concentrated solution containing 700 mg/dl of DDI prepared in a similar manner as in Example 1, and 250 ml of water was passed through the column (at SV=2) to obtain Fraction I'. Subsequently, 200 ml of aqueous 10% isopropanol alcohol solution was passed through the column (at SV=2) to obtain Fraction II'. The treatments with said resin were carried out at a temperature of 30° C.

The thus obtained fractions were analyzed by liquid chromatography. Fraction I' contained Ura and Hyp, which were recovered at a percentage of 99% and 97%, respectively. Fraction II' contained DDI and DDU, which were recovered at a percentage of 98% and 95%, respectively.

The pH of Fraction II' was adjusted to 8 by the addition of 1N NaOH, and the fraction was then concentrated to crystallize DDI. There was obtained 440 mg of crystals of highly pure DDI. The results of elemental analysis of the thus obtained DDI are shown in Table 6.

TABLE 6

| | Elemental Analysis | | |
|---|---|---|---|
| | C | H | N |
| Calculated: | 50.84% | 5.12% | 23.72% |
| Found: | 50.87% | 5.10% | 23.81% |

EXAMPLE 9

Into shouldered 500 ml flasks was charged 50 ml each of a culture medium (pH=7.0) containing 0.5 g/dl of a yeast extract, 1.0 g/dl of peptone, 1.0 g/dl of a meat extract and 0.5 g/dl of NaCl, and the contents of the flasks were sterilized. One platinum loopful of Escherichia coli ATCC (10798), which had been cultured on a bouillon agar medium at 30° C. for 16 hours, was inoculated in each medium contained in the flasks and cultured with shaking at 30° C. for 16 hours. The cells were separated from the medium by centrifugation and washed with 0.05 M phosphate buffer (pH=7.0). The cells were again separated by centrifugation to prepare washed cells.

The washed cells of Escherichia coli ATCC (10798) were added to 1 liter of 100 mM phosphate buffer (pH=7.0) containing 20 mM of DDU and 20 mM of Ad, whereby the concentration of the cells in said medium was 1% by weight. The reaction was allowed to proceed at 50° C. for 24 hours. As a result, there was produced 85 mg/dl of DDA (recovering rate=18%).

The cells were removed off by centrifugation (at 7,000 G for 40 minutes), and then 50 mg of activated carbon (Shirasagi Charcoal, manufactured by Takeda Chemical Industries Co., Ltd.) was added after adjusted to pH=8.0 by NaOH solution thereto. The resulting mixture was maintained at 50° C. for 1 hour, so as to remove off proteins and to effect decoloration, and then filtered, using a filter having a pore size of 0.45 μm. The filtrate was concentrated to 15 ml and then filtered, using a No. 5 filter paper. Thirteen (13) grams of the concentrated solution, which contained 6.2 g/dl of DDA, was fed at an SV of 1 to a column having a diameter of 20 mm and a height of 210 mm and charged with a porous nonpolar synthetic adsorbing resin (SP 207, manufactured by Mitsubishi Chemical Industries, Ltd.), and then 260 ml of water was passed through the column at an SV of 2. The thus obtained fraction is designated as Fraction I. Subsequently, 390 ml of aqueous 10% ethyl alcohol solution was passed (at SV=2) to carry out elution. The thus obtained fraction is designated as Fraction II. Thereafter, 390 ml of aqueous 20% ethyl alcohol solution was passed through the column (at SV=2) to effect additional elution. The thus obtained fraction is designated as Fraction III.

The fractions were analyzed by liquid chromatography. In Faction I was contained U alone, the recovering rate of which was 99%. In Fraction II were contained Ad, DDU and a small quantity of DDA, the recovering rates of Ad and DDU being 99% and 98,—respectively. In Fraction III was contained DDA, the recovering rate of which was 95%.

Fraction III was concentrated to crystallize DDA. It was cooled to 10° C. and filtered to obtain 600 mg of highly pure DDA. The results of elemental analysis of the thus obtained DDA are shown in Table 7.

TABLE 7

| | Elemental Analysis | | | |
|---|---|---|---|---|
| | C | H | N | O |
| Calculated: | 51.06% | 5.57% | 29.77% | 13.60% |
| Found: | 51.22% | 5.53% | 29.78% | 13.47% |

EXAMPLE 10

To a column having a diameter of 20 nm and a height of 210 mm and charged with 65 ml of a porous nonpolar synthetic adsorption resin (SP 207, manufactured by Mitsubishi Chemical Industries, Ltd.) was fed (at SV=2) 13 ml of concentrated DDA-containing solution containing 6.2 g/dl of DDA prepared in a similar manner as in Example 1, and 260 ml of water was passed through the column (at SV=2)to obtain Fraction I'. Subsequently, 520 ml of aqueous 20% methyl alcohol solution was passed through the column (at SV=2) to carry out elution. The fraction obtained was designated as Fraction II'. Thereafter, 390 ml of aqueous 40% methyl alcohol solution was passed (at SV=2) to effect additional-elution. The thus obtained fraction is designated as Fraction III'.

The thus obtained fractions were analyzed by liquid chromatography. In Fraction I' was contained U alone, the recovering rate of which was 98%. In Fraction II'were contained Ad, DDU and a small quantity of DDA, the recovering rates of Ad and DDU being 98% and 98%, respectively. In Fraction III' was contained DDA, the recovering rate of which was 93%.

Fraction III' was concentrated to crystallize DDA. It was cooled to 10° C. and then filtered to obtain 580 mg of highly pure DDA. The results of elemental analysis of the thus obtained DDA are shown in Table 8.

TABLE 8

| | Elemental Analysis | | | |
|---|---|---|---|---|
| | C | H | N | O |
| Calculated: | 51.06% | 5.57% | 29.77% | 13.60% |
| Found: | 51.30% | 5.53% | 29.80% | 13.37% |

As described hereinabove, the process of the invention makes it possible to separate and purify DDA in an effective manner by means of a treatment with a porous nonpolar resin. It can therefore be practiced commercially.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A process for the purification of a 2',3'-dideoxynucleoside from a solution obtained from a process requiring a microorganism or an enzyme, said solution containing, as impurities, other 2',3'-dideoxynucleosides or nucleic acid bases, said process comprising:

(i) contacting said solution with a porous, nonpolar resin to cause the adsorption of said 2',3'-dideoxynucleoside onto said porous nonpolar resin, wherein said 2',3'-dideoxynucleoside is 2',3'-dideoxyadenosine or 2',3'-dideoxyinosine;

(ii) separating said porous nonpolar resin from said solution; and (iii) fractionally eluting said adsorbed 2',3'-dideoxynucleoside to obtain a purified 2',3'-dideoxynucleoside product.

2. The process of claim 1, wherein said porous nonpolar resin is a styrene-divinylbenzene resin.

3. The process of claim 1, wherein said porous nonpolar resin is a modified styrene-divinylbenzene resin.

4. The process of claim 1, wherein said 2',3'-dideoxynucleoside is 2',3'-dideoxyadenosine.

5. The process of claim 4, wherein said porous nonpolar resin is a styrene-divinylbenzene resin.

6. The process of claim 4, wherein said porous nonpolar resin is a modified styrene-divinylbenzene resin.

7. The process of claim 1, wherein said 2',3'-dideoxynucleoside is 2',3'-dideoxyinosine.

8. The process of claim 7, wherein said porous nonpolar resin is a styrene-divinylbenzene resin.

9. The process of claim 7, wherein said porous nonpolar resin is a modified styrene-divinylbenzene resin.

10. The process of claim 1, said solution containing, as impurities, said other 2',3'-dideoxynucleosides and said nucleic acid bases.

11. The process of claim 4, said solution containing, as impurities, uracil and 2',3'-dideoxyuridine.

12. The process of claim 7, said solution containing, as impurities, uracil and 2',3'-dideoxyuridine.

13. The process of claim 4, said solution containing, as impurities, adenine, uracil and 2',3'-dideoxyuridine.

14. The process of claim 7, said solution containing, as impurities, uracil, 2',3'-dideoxyuridine and hypoxanthine.

15. The process of claim 4, said solution containing, as impurities, adenine.

16. The process of claim 7, said solution containing as impurities, hypoxanthine.

* * * * *